United States Patent [19]

Jones et al.

[11] 4,342,765

[45] Aug. 3, 1982

[54] GUANIDINE DERIVATIVES AND PHARMACEUTICAL COMPOSITIONS CONTAINING THEM

[75] Inventors: Derrick F. Jones, Macclesfield; Keith Oldham, Cheadle, both of England

[73] Assignee: Imperial Chemical Industries Limited, London, England

[21] Appl. No.: 112,608

[22] Filed: Jan. 16, 1980

[30] Foreign Application Priority Data

Jan. 18, 1979 [GB] United Kingdom ............... 7901872

[51] Int. Cl.³ .................. C07D 277/20; C07D 263/30
[52] U.S. Cl. .................................. 424/249; 424/269; 424/263; 424/270; 548/128; 548/133; 548/194; 548/195; 548/196; 548/198; 548/233; 424/251; 544/182; 544/321; 546/275; 546/276; 546/277; 546/280
[58] Field of Search .............. 424/270, 273, 263, 269, 424/249, 270, 251, 272; 548/198, 128, 133, 194, 195, 196, 233

[56] References Cited

U.S. PATENT DOCUMENTS

| | | | |
|---|---|---|---|
| 3,876,647 | 4/1975 | Durant et al. | 424/263 |
| 3,897,444 | 7/1975 | Durant et al. | 260/306.8 R |
| 3,905,984 | 9/1975 | Durant et al. | 260/294.84 |
| 3,920,822 | 11/1975 | Durant et al. | 424/263 |
| 3,932,427 | 1/1976 | Durant et al. | 260/295 E |
| 3,950,333 | 4/1976 | Durant et al. | 260/302 A |
| 3,950,353 | 4/1976 | Durant et al. | 260/307 R |
| 3,975,530 | 8/1976 | Durant et al. | 424/270 |
| 4,018,391 | 4/1977 | Durant et al. | 424/269 |
| 4,018,928 | 4/1977 | Durant et al. | 424/263 |
| 4,018,931 | 4/1977 | Durant | 424/269 |
| 4,022,797 | 5/1977 | Durant et al. | 260/302 R |
| 4,038,408 | 7/1977 | Durant et al. | 424/270 |
| 4,049,672 | 9/1977 | Durant et al. | 548/342 |
| 4,053,473 | 10/1977 | Durant et al. | 548/329 |
| 4,062,863 | 12/1977 | Ganellin et al. | 260/306.8 R |
| 4,104,382 | 8/1978 | Black et al. | 424/270 |
| 4,112,104 | 9/1978 | Durant et al. | 424/270 |
| 4,165,377 | 8/1979 | Jones et al. | 424/273 |
| 4,165,378 | 8/1979 | Gilman et al. | 424/270 |

FOREIGN PATENT DOCUMENTS

| | | |
|---|---|---|
| 1493931 | 11/1977 | United Kingdom . |
| 1496787 | 5/1978 | United Kingdom . |
| 832660 | 2/1976 | Belgium . |
| 1497260 | 5/1978 | United Kingdom . |
| 832661 | 2/1976 | Belgium . |
| 832662 | 2/1976 | Belgium . |
| 832663 | 2/1976 | Belgium . |
| 832664 | 2/1976 | Belgium . |
| 832665 | 2/1976 | Belgium . |
| 841526 | 11/1976 | Belgium . |
| 843814 | 11/1976 | Belgium . |
| 843839 | 1/1977 | Belgium . |
| 843840 | 1/1977 | Belgium . |
| 844503 | 1/1977 | Belgium . |
| 844504 | 1/1977 | Belgium . |
| 846452 | 3/1977 | Belgium . |
| 2604056 | 5/1976 | Fed. Rep. of Germany . |
| 53-141271 | 12/1978 | Japan . |
| 1305546 | 2/1973 | United Kingdom . |
| 1305548 | 2/1973 | United Kingdom . |
| 1305549 | 2/1973 | United Kingdom . |
| 1307539 | 2/1973 | United Kingdom . |
| 1338169 | 11/1973 | United Kingdom . |
| 1341375 | 12/1973 | United Kingdom . |
| 1341376 | 12/1973 | United Kingdom . |
| 1395929 | 5/1975 | United Kingdom . |
| 1397436 | 6/1975 | United Kingdom . |
| 1398426 | 6/1975 | United Kingdom . |
| 1399283 | 7/1975 | United Kingdom . |
| 1400319 | 7/1975 | United Kingdom . |
| 1419994 | 1/1976 | United Kingdom . |
| 1421792 | 1/1976 | United Kingdom . |
| 1421999 | 1/1976 | United Kingdom . |
| 1422408 | 2/1976 | United Kingdom . |
| 1431589 | 4/1976 | United Kingdom . |

*Primary Examiner*—Nicholas S. Rizzo
*Attorney, Agent, or Firm*—Cushman, Darby & Cushman

[57] ABSTRACT

Guanidine derivatives which are histamine H-2 antagonists and which inhibit gastric acid secretion. These derivatives have the formula:

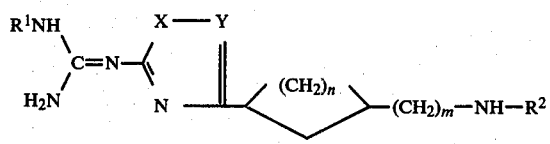

in which
X is oxygen or sulphur;
Y is nitrogen or a CH radical;
n is 1, 2, 3 or 4;
m is 0 or 1;
$R^1$ is, for example, hydrogen or alkyl of 1-6 carbons; and
$R^2$ is, for example,

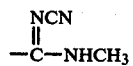

and are characterized by the guanidino and cycloalkyl substituents which are attached directly to the heterocyclic ring.

10 Claims, No Drawings

GUANIDINE DERIVATIVES AND PHARMACEUTICAL COMPOSITIONS CONTAINING THEM

This invention relates to guanidine derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.*, 1966, 27, 427) and the action of histamine at this receptor is blocked (antagonised) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In Belgian Pat. Nos. 866155 and 866156 there are described histamine H-2 receptor antagonists which are guanidinooxazole, -thiazole and -imidazole derivatives having a side chain to the end of which is attached, for example, a urea, thiourea, guanidine or N-cyanoguanidine residue. It has now been discovered that if a cycloalkyl residue is inserted into the side chain of such molecules, there are produced compounds which are potent H-2 receptor antagonists.

According to the invention there is provided a guanidine derivative of the formula:

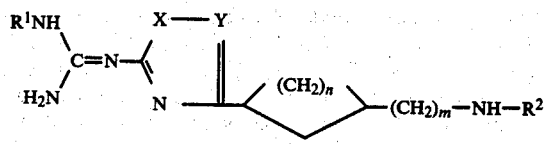

in which X is an oxygen or sulphur atom;
Y is a nitrogen atom or a CH radical;
n is 1, 2, 3 or 4;
m is 0 or 1;
$R^1$ is a hydrogen atom, an alkyl radical of 1 to 6 carbon atoms or an alkoxyalkyl radical of 3 to 10 carbon atoms in which the oxygen atom is separated from the nitrogen atom of the guanidine residue by at least two carbon atoms;
$R^2$ is a radical of the formula —A—B in which A is a 3,4-dioxocyclobuten-1,2-diyl radical or a radical of the formula C=Z in which Z is an oxygen or sulphur atom or a radical of the formula NCN, NNO$_2$, CHNO$_2$, NCONH$_2$, C(CN)$_2$, NCOR$^3$, NCO$_2$R$^3$, NSO$_2$R$^3$ or NR$^4$ in which R$^3$ is an alkyl radical of 1 to 6 carbon atoms, a phenyl radical or a monocyclic heteroaromatic ring containing one or two hetero atoms selected from oxygen nitrogen and sulphur atoms and R$^4$ is a hydrogen atom or an alkyl radical of 1 to 6 carbon atoms;
B is an alkyl, alkoxy or alkylthio radical of 1 to 6 carbon atoms or a radical of the formula NHR$^5$ in which R$^5$ is a hydrogen atom or an alkyl radical of 1 to 6 carbon atoms, an alkenyl or alkynyl radical of 3 to 10 carbon atoms in which the double or triple bond is separated from the nitrogen atom of NHR$^5$ by at least one carbon atom, a cycloalkyl radical of 3 to 6 carbon atoms, a (primary hydroxy)alkyl or (primary amino)alkyl radical of 2 to 6 carbon atoms; a heteroalkyl radical of 1 to 6 carbon atoms, an alkoxyalkyl radical of 3 to 6 carbon atoms in which the oxygen atom is separated from the nitrogen atom of NHR$^5$ by at least two carbon atoms, a phenylalkyl or monocyclic aromatic heterocyclylalkyl radical in which the alkyl part is of 1 to 6 carbon atoms, the phenyl ring carries an optional halogen atom and the heterocyclic ring contains one or two hetero atoms selected from oxygen, nitrogen and sulphur atoms; or R$^5$ is a benzoylaminoalkyl or benzenesulphonylaminoalkyl radical in which the alkyl part is of 2 to 6 carbon atoms and the benzene ring carries an optional chlorine substituent, or a radical of the formula:

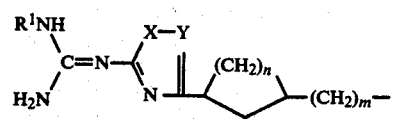

II

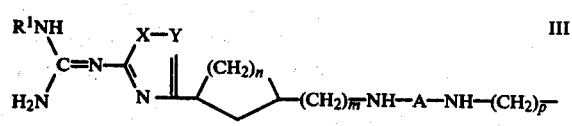

III

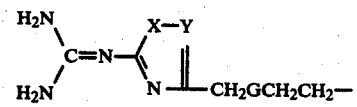

IV

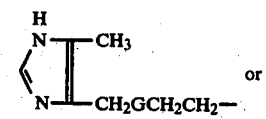

V or

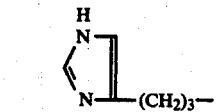

VI in which X, Y, n, m and $R^1$ have the meanings given above, p is 2 to 12 and G is a sulphur atom or a methylene radical; or $R^2$ is a radical of the formula:

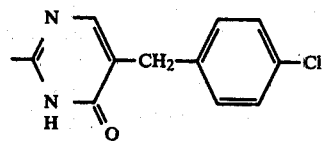

VII

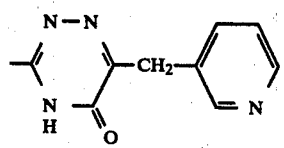

VIII or

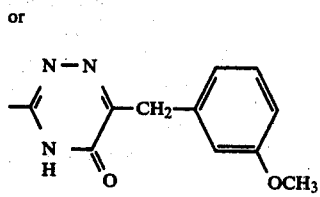

IX and the pharmaceutically-acceptable acid-addition salts thereof.

It is to be understood that in the above formulae and throughout this specification, although the double bonds in both side chains have been inserted in particular positions, various other tautomeric forms are possible, and this invention includes such tautomeric forms within its scope, both in terms of the compound of the invention and in terms of the manufacturing processes. It is also to be understood that in formulae I, II and III, the groups attached to the alicyclic ring may be in the cis or trans configuration.

It will be observed that the compound of the formula I contains at least two asymmetric centres, namely those carbon atoms of the alicyclic ring which are substituted. Each individual isomer of the formula I may therefore be resolved into two optically active enantiomers. The biological activity, as hereinafter defined, of the enantiomers may differ and it is therefore to be understood that this invention encompasses the racemic form of the compound of the formula I, and in addition any optical isomer which possesses the useful properties of the compound of the invention, it being a matter of common general knowledge to those skilled in the art how such isomers may be separated and their biological properties determined.

A particular value for $R^1$ when it is an alkyl radical is a methyl, ethyl or n-butyl radical.

A particular value for $R^1$ when it is an alkoxyalkyl radical is a 2-methoxyethyl radical.

A particular value for $R^3$ or $R^4$ when it is an alkyl radical is a methyl radical.

A particular value for $R^3$ when it is a heteroaromatic ring is a pyridyl radical, for example a 3-pyridyl radical.

A particular value for B when it is an alkyl, alkoxy or alkylthio radical is a methyl, methoxy, ethoxy or methylthio radical.

A particular value for $R^5$ is a hydrogen atom or a methyl, ethyl, allyl, propargyl, 2-hydroxyethyl, 2-amino-ethyl, trifluoromethyl, 2-methoxyethyl, benzyl, 2-phenylethyl, 2-(4-chlorophenyl)ethyl, pyrid-3-ylmethyl, 2-benzoylaminoethyl, 2-(2-chlorobenzoylamino)ethyl or 2-benzene-sulphonylaminoethyl radical.

The following are preferred features of the guanidine derivative of the formula I. When any of these features is taken, either singly or in combination, with the other general features of the guanidine derivative of the formula I listed above, there are obtained preferred sub groups of compounds within the above definition.

1. The groups attached to the alicyclic ring are in the cis configuration.
2. $R^1$ is a hydrogen atom or an alkoxyalkyl radical, for example a 2-methoxyethyl radical.
3. X is a sulphur atom and Y is a CH radical.
4. n is 2 or 3.
5. m is 0.
6. $R^2$ is a radical of the formula A-B in which A is a radical of the formula C=Z in which Z is a radical of the formula NCN, $NNO_2$, $CHNO_2$ or $NSO_2CH_3$.
7. $R^2$ is a radical of the formula —A—B in which B is a radical of the formula $NHR^5$ in which $R^5$ is an alkyl or a (primary amino)alkyl radical, for example a methyl or 2-aminoethyl radical.
8. —$R^2$ is a radical of the formula VII, VIII or IX given above.

The following compounds are preferred:

2-guanidino-4-[3-(2-cyano-3-methylguanidino)cyclopentyl]thiazole (Example 16);
2-guanidino-4-[3-(3-methylthioureido)cyclopentyl]thiazole (Example 26);
2-guanidino-4-{3-[3-cyano-2-(2-aminoethyl)guanidino]cyclohexyl}thiazole (Example 31);
2-[2-(2-methoxyethyl)guanidino]-4-[3-(3-methylthioureido)cyclohexyl]thiazole (Example 40);
1-{3-[2-((2-methoxyethyl)guanidino)thiazol-4-yl]cyclohexylamino}-1-methylamino-2-nitroethylene (Example 41); and the pharmaceutically-acceptable acid-addition salts thereof.

A particular pharmaceutically-acceptable acid-addition salt of the guanidine derivative of the invention is, for example, a salt formed with hydrochloric, hydrobromic, phosphoric, sulphuric, acetic, citric or maleic acid.

The guanidine derivative of the invention may be manufactured by methods known in themselves for the manufacture of chemically-analogous compounds. The following processes, X, Y, m, n, $R^1$ and $R^2$ having the meanings stated above unless indicated otherwise, are therefore provided as further features of the invention.

The process of the invention is characterised by:

(a) for those compounds in which —$R^2$ is a radical of the formula —A—B in which B is other than an alkyl radical, reaction of a compound of the formula:

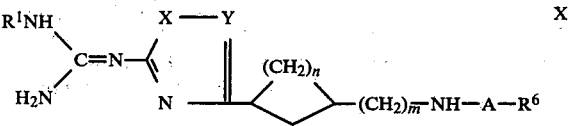

in which $R^6$ is a displaceable radical with a compound of the formula B-H;

(b) for those compounds in which —$R^2$ is a radical of the formula —A—B in which A is a radical of the formula C=Z in which Z is a sulphur or oxygen atom and B is a radical of the formula $NHR^5$ in which $R^5$ is a hydrogen atom or an alkyl, alkenyl, alkynyl, haloalkyl, alkoxyalkyl, optionally-substituted phenylalkyl or monocyclic aromatic heterocyclylalkyl radical or a radical of the formula II, III, IV, V or VI, reaction of a compound of the formula:

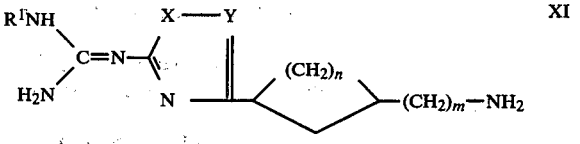

with a compound of the formula $R^7$—N=C=D in which $R^7$ is a hydrogen atom or an alkyl, alkenyl, alkynyl, haloalkyl, alkoxyalkyl, optionally-substituted phenylalkyl or monocyclic aromatic heterocyclylalkyl radical or a radical of the formula II, III, IV, V or VI and D is a sulphur or oxygen atom;

(c) reaction of a compound of the formula III with a compound of the formula:

in which $R^6$ is a displaceable radical;

(d) for those compounds in which —$R^2$ is a radical of the formula —A—B in which B is a radical of the formula NHR⁵ in which R⁵ is an optionally-substituted benzoylaminoalkyl or benzenesulphonylaminoalkyl radical, reaction of a compound of the formula:

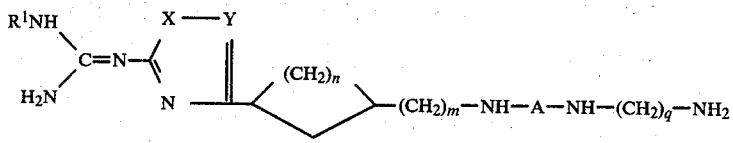

in which q is 2 to 6, with an acid, or an activated derivative of an acid, of the formula:

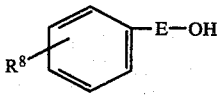  XIV in which R⁸ is a hydrogen or chlorine atom and E is a radical of the formula CO or SO₂;

(e) for those compounds in which —R² is a radical of the formula —A—B in which A is a radical of the formula C=Z in which Z is a sulphur or oxygen atom and B is a radical of the formula NHR⁵ in which R⁵ is a hydrogen atom or an alkyl, alkenyl, alkynyl, cycloalkyl, haloalkyl, alkoxyalkyl, optionally-substituted phenylalkyl or monocyclic aromatic heterocyclylalkyl radical or a radical of the formula II, III, IV, V or VI, reaction of a compound of the formula:

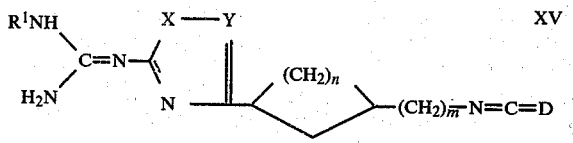 XV in which D is an oxygen or sulphur atom with a compound of the formula R⁷-NH₂ in which R⁷ has the value given in process (b) above;

(f) for those compounds in which —R² is a radical of the formula —A—B in which A is a radical of the formula C=Z in which Z is an oxygen atom or an NH radical and B is a radical of the formula NHR⁵, addition of water or ammonia to a carbodiimide of the formula:

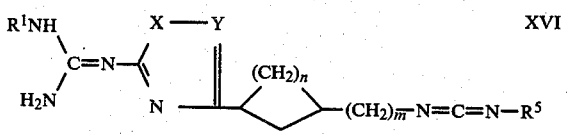 XVI or (g) for those compounds in which —R² is a radical of the formula —A—B in which A is a radical of the formula C=Z in which Z is a radical of the formula NCN and B is a radical of the formula NHR⁵ in which R⁵ is a hydrogen atom, reaction of a compound of the formula XI with dicyanimide:

Whereafter if a salt is required, the compound of the formula I in free base form is reacted with an acid which affords a pharmaceutically-acceptable anion.

Process (a) may be carried out by using an excess of B-H, that is using excess of the amine R⁵NH, optionally in the presence of a diluent or solvent such as water, methanol, ethanol, chloroform or pyridine or a mixture of any of these, at ambient temperature or at an elevated temperature, for example up to the boiling point of the diluent or solvent for a period of between 1 and 100 hours, or alternatively using an excess of the alcohol

XIII

R⁹—OH or alkylthiol R⁹—SH in which R⁹ is an alkyl radical of 1 to 6 carbon atoms, preferably in the form of a salt such as the sodium salt in the same alcohol or alkylthiol as diluent or solvent. R⁶ is preferably an alkoxy or alkylthio radical, for example such a radical of 1 to 6 carbon atoms, for example a methoxy, ethoxy or methylthio radical.

Process (b) may be carried out using a molar equivalent or excess of the compound R⁷—N=C=D. When D is a sulphur atom the reaction is preferably carried out in a diluent or solvent such as methanol, ethanol or dimethylformamide. When D is an oxygen atom, a non-alcoholic diluent or solvent must be used. The reaction may be accelerated or completed by the application of heat, for example by heating to the boiling point of the diluent or solvent.

Process (c) may be carried out using a molar equivalent or excess of the compound of the formula XII in the presence of a diluent or solvent such as methanol, ethanol or acetonitrile, at ambient temperature or at a temperature up to the boiling point of the diluent or solvent, for a period of between 1 and 24 hours. R⁶ is preferably an alkoxy or alkylthio radical, for example such a radical of 1 to 6 carbon atoms, for example a methoxy, ethoxy or methylthio radical.

Process (d) may be carried out in a diluent or solvent such as methanol, ethanol or pyridine, preferably at ambient temperature. A preferred activated derivative of the acid of the formula XIV is the acid chloride.

Process (e) may be carried out in the same way as process (b).

Process (f) may be carried out in a diluent or solvent such as dimethyl formamide or aqueous dimethyl formamide, at ambient temperature. The carbodiimide of the formula XVI is preferably prepared in situ, for example by reaction of the corresponding thiourea with silver nitrate. In such a case, at the end of the reaction, the excess silver ions are conveniently removed from solution by precipitation as the sulphide.

When X is a sulphur atom or an NH radical and Y is a CH radical, the starting material of the formula XI may be prepared by protection of the amino group in the compound of the formula:

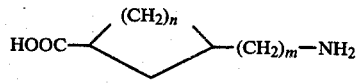 XVII for example as the phthalimide, elaboration of the carboxy group to a halomethyl ketone, reaction of this ketone with the appropriately-substituted amidinothiourea or amidinoguanidine and finally removal of the protecting group, for example as set out in Example 1, 10, 16 or 40.

When X is an oxygen atom and Y is a CH radical, the starting material of the formula XI may be similarly prepared, by analogy with the methods of preparation of 2-guanidinooxazoles described in Belgian Pat. No. 866,155.

When X is a sulphur or oxygen atom and Y is a nitrogen atom, the starting material of the formula XI may be similarly prepared, by analogy with the methods of preparation of 5-guanidino-1,2,4-thiadiazole and 5-guanidino-1,2,4-oxadiazoles described in European Patent Publications Nos. 0006679 and 0006286 respectively.

The starting material of the formula X may be prepared by reaction of the starting material of the formula XI with a compound of the formula:

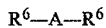  XVIII in which $R^6$ is a displaceable radical, for example as set out in Examples 1, 5, 9, 10, 13, 16, 17, 27, 29 or 41.

The starting material of the formula XV may be prepared by reaction of the compound of the formula XI with carbonyldiimidazole or thiocarbonyldiimidazole, for example as set out in Example 34.

As noted above, the guanidine derivative of the invention is a histamine H-2 antagonist, inhibits the secretion of gastric acid in warm-blooded animals and is therefore useful in the treatment of peptic ulcers and other conditions caused by exacerbated by gastric acidity, including stress ulcers and gastro-intestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in a thermostatically-controlled (30° C.) tissue bath (25 ml.) containing oxygenated (95% $O_2$; 5% $CO_2$) Krebs-Hanseleit buffer (pH 7.4). The tissue is allowed to stabilise over 1 hour during which time it is washed 2–4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 $\mu$M.

The histamine-stimulated cyclic AMP test is carried out as described by Scholes et al., *Agents and Actions*, 1976, 6, 677–682.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (9–12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mole/kg/hour of histamine or 2 $\mu$g/kg/hour pentagastrin) in saline (15 ml./hour) is begun. Gastric acid samples are collected every 15 minutes. The volume of each sample is measured and a 1 ml. aliquot is titrated to neutrality with 0.1 N NaOH to determine acid concentration. When a plateau of secretion is reached, (1–2 hours) the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark), is instilled into the stomach through a fistula dosing plug. One hour later, the fistula is re-opened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test and/or the histamine stimulated cyclic AMP test are predictive of activity in the dog test. No overt toxicity or side effects were noted during the dog tests.

Some of the guanidine derivatives of the invention, and in particular those in which —$R^2$ is a radical of the formula VII, VIII or IX, are also histamine H-1 antagonists and this effect may be demonstrated on standard test systems such as the guinea pig ileum. A compound having such a property is useful for the treatment of conditions involving an immune reaction, for example allergic conditions.

Many of the actions of histamine are mediated by histamine H-1 and H-2 receptors and a compound combining both H-1 and H-2 antagonist properties is useful for the treatment of certain states, for example inflammation and the inhibition of the effects of histamine on blood pressure and the prevention and treatment of anaphylactic shock.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purpose it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminum hydroxide-magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical antihistamines (histamine H-1-antagonists), for example mepyramine or diphenhydramine and/or one or more steroidal anti-inflammatory agents, for example fluocinolone or triamcinolone.

A topical formulation may contain 1–10% w/w of the heterocyclic derivative of the invention. A preferred pharmaceutical composition of the invention is one suitable for oral administration in unit dosage form, for example a tablet or capsule which contains between 10 mg. and 500 mg. of the heterocyclic derivative, or one suitable for intravenous, subcutaneous or intramuscular injection, for example a sterile injectable containing between 0.1% and 10% w/w of the heterocyclic derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each patient will receive an oral dose of between 15 mg. and 1500 mg., and preferably between 20 mg. and 200 mg., of guanidine derivative or an intravenous, subcutaneous or intramuscular dose of between 1.5 mg. and 150 mg., preferably between 5 mg. and 20 mg., of the guanidine derivative, the composition being administered 2 to 4 times per day. The rectal dose will be approximately the same as the oral dose. The composition may be administered less frequently when it contains an amount of heterocyclic derivative which is a multiple of the amount which is effective when given 2–4 times per day. When employing the H-1 or H-1/H-2 antagonist properties of the pharmaceutical composition of the invention, the same dose levels as are described above may be used. The invention is illustrated, but not limited by the following Examples in which the temperatures are in degrees Centigrade. The n.m.r. resonances are expressed in $\delta$ with respect to tetramethylsilane as an internal standard ($\delta=0$). The following contractions are used s=singlet
d=doublet
t=triplet
m=multiplet
br=broad

EXAMPLE 1

To a stirred solution of 2-guanidino-4-(3-aminocyclohexyl)thiazole (0.25 g.) in methanol (10 ml.) was added dimethyl (cyanoimido)dithiocarbonate (0.15 g.) and the mixture allowed to stand overnight. The residue, obtained on evaporation of methanol, was subjected to preparative thin layer chromatography on silica gel GF (Uniplate, Analtech Inc., Delaware, USA) using chloroform/methanol (90:10 v/v) for development. Isolation of the appropriate region of the chromatogram and elution with warm ethanol/chloroform (50:50 v/v) and crystallisation of the material extracted from methanol ether gave 2-guanidino-4-[3-(3-cyano-2-methylisothioureido)-cyclohexyl]thiazole, m.p. 216°–218° (decomp.).

The 2-guanidino-4-(3-aminocyclohexyl)thiazole used as starting material may be prepared as follows:

A mixture of cis-3-aminocyclohexane carboxylic acid (30.4 g.), phthalic anhydride (31.4 g.) and glacial acetic acid (75 ml.) in dimethylformamide (150 ml.) was heated under reflux for 1 hour. After cooling, the reaction mixture was poured into water (1.2 l.) and the precipitated 3-phthalimidocyclohexane carboxylic acid (49.7 g.) collected and dried.

To this acid (12 g.) was added thionyl chloride (25 ml.) and the mixture heated under reflux for 1.5 hours to give 3-phthalimidocyclohexanoyl chloride which was obtained as a brown, viscous oil after evaporation of the excess thionyl chloride.

This acid chloride (12.8 g.) was dissolved in dry ether (60 ml.) and the solution added dropwise to a dry solution of diazomethane in ether (prepared from 32 g. of 'Diazald' at −60°). After standing for 0.25 hours at −60°, the reaction mixture was allowed to achieve ambient temperature and allowed to stand overnight. The precipitated crystalline diazoketone (m.p. 128°–130°) was collected, washed with ether and dried.

A slurry of the diazoketone (11 g.) in acetone (75 ml.) was treated with concentrated hydrochloric acid, dropwise, until effervescence ceased. The reaction mixture was poured into water (100 ml.) and the precipitated solid collected and washed with water and dried to give 1-chloroacetyl-3-phthalimidocyclohexane (11 g.), m.p. 113°–115°.

This chloroketone (7.0 g.), dissolved in hot ethanol (250 ml.) was added to a suspension of amidinothiourea (2.8 g.) in boiling ethanol (150 ml.) and the mixture heated under reflux for 1 hour. The resulting solution was concentrated by evaporation under reduced pressure and the concentrate diluted with ether until turbidity persisted. On standing crystalline 2-guanidino-4-(3-phthalimidocyclohexyl)thiazole hydrochloride (10 g.) was deposited.

This material (5 g.) was added to a mixture of acetic acid (19 ml.) and concentrated hydrochloric acid (19 ml.) and the mixture heated on a steam bath, under a reflux condenser, overnight. The reaction mixture was evaporated to dryness under reduced pressure and the residue stirred for 5 minutes with a mixture of water (60 ml.) and ethyl acetate (60 ml.). The aqueous layer was separated, extracted with ethyl acetate (3×60 ml.) and evaporated to dryness. The solid residue was crystallised from a methanol-ether mixture to give 2-guanidino-4-(3-aminocyclohexyl)thiazole dihydrochloride. This crystalline material (3.5 g.) was dissolved in water (20 ml.) and the solution basified with 3 N sodium hydroxide. Crystalline 2-guanidino-4-(3-aminocyclohexyl)thiazole (2.0 g.) was collected, washed thoroughly with ice water and dried.

EXAMPLE 2

A suspension of 2-guanidino-4-[3-(3-cyano-2-methylisothioureido)cyclohexyl]thiazole (0.5 g.) in ethanol (10 ml.) was treated with a solution of methylamine in ethanol (33% w/v; 30 ml.) and the mixture stirred overnight at room temperature. The residue, obtained on evaporation of the reaction mixture, was subjected to preparative thin layer chromatography on silica gel GF 254 plates (Merck) using chloroform/methanol/ammonia (s.g. 0.88) (8:25:0.6 v/v/v) for development. Extraction of the appropriate region of the chromatogram with ethanol/chloroform 50:50 v/v gave 2-guanidine-4-[3-(2-cyano-3-methylguanidino)cyclohexyl]-thiazole as a glass. The n.m.r. spectrum in $d_6$ dimethylsulphoxide included resonances at 1.2–2.2(m,9H), 2.7(d,3H) 4.2(br m, 1H), 6.2(s,1H) 6.5(d,1H) and 6.8(br s,5H).

EXAMPLE 3

To a solution of 2-guanidino-4-(3-aminocyclohexyl)-thiazole (0.6 g.) in ethanol (20 ml) was added methylisothiocyanate (0.18 g.) and the resulting solution was heated under reflux for two hours. The residue obtained on evaporation of the ethanol was subjected to column chromatography on silica gel (Kieselgel 60, Merck) using chloroform/methanol/ammonia (s.g. 0.88) 8:2:0.3 v/v/v for development. The product, 2-guanidino-4-[3-(3-methylthioureido)cyclohexyl]thiazole, (0.4 g.) was obtained as a glass. The n.m.r. spectrum, in $d_6$ dimethylsulphoxide, included resonances at 1.2–2.2(m,9H);2.8(d,3H); 4.0(m,1H); 6.2(s,1H); 6.8(br s,4H); and 7.2(br d,2H).

EXAMPLE 4

A mixture of 2-guanidino-4-(3-aminocyclohexyl)-thiazole dihydrochloride (0.62 g.), triethylamine (0.56 ml.) and sodium dicyanamide (0.23 g.) in n-butanol (10 ml.) was heated under reflux for four hours. The filtered reaction mixture was evaporated and the residue subjected to preparative thin layer chromatography on silica GF 254 (Merck) plates using chloroform/methanol/ammonia (s.g. 0.88) 8:2:03 v/v/v for development. Isolation of the appropriate region of the chromatogram and elution with hot ethanol/chloroform (50:50 v/v) gave 2-guanidino-4-[3-(2-cyanoguanidino)-cyclohexyl] thiazole as a glass. The n.m.r. spectrum in $d_6$ dimethylsulphoxide included resonances at 1.28(m); 1.8(m); 6.3(s); 6.55(br s); 6.67(d); 6.9(br s) and showed resonances attributable to solvation by ethanol (~0.5 mole) and water.

EXAMPLE 5

A solution of 2-guanidino-4-(3-aminocyclohexyl)-thiazole (0.5 g.) in boiling acetonitrile (25 ml.) was treated with 1,1-di(methylthio)-2-nitroethylene (0.35 g.) and the mixture heated under reflux for 7 hours. The reaction mixture was evaporated to dryness and the residue crystallised from methanol to give 1-[3-(2-guanidinothiazol-4-yl)cyclohexylamino]-1-methylthio-2-nitroethylene (0.5 g.) as a yellow solid. The n.m.r. spectrum in $d_6$ dimethylsulphoxide included signals at 1.2–2.2(m) 3.3(s), 3.7(m), 6.27(s), 6.65(s) and 6.69(br s)

EXAMPLE 6

A solution of 1-[3-(2-guanidinothiazol-4-yl)cyclohexylamino]-1-methylthio-2-nitroethylene (0.25 g.) in a warm mixture of methanol (20 ml.) and chloroform (10 ml.) was treated with 30 ml. of a solution of methylamine in ethanol (33% w/v) and the resulting solution allowed to stand at room temperature for 5 hours. Evaporation of the reaction mixture and crystallisation of the residue from methanol gave 0.19 g. of 1-[3-(2-guanidinothiazol-4-yl)cyclohexylamino]-1-methylamino-2-nitroethylene, m.p. 218°–221° (decomp.).

EXAMPLE 7

A solution of 1-[3-(2-guanidinothiazol-4-yl)cyclohexylamino]-1-methylthio-2-nitroethylene (0.25 g.) in a warm mixture of methanol (50 ml.) and chloroform (15 ml.) was treated with 2-methoxyethylamine (5 ml.) and the solution allowed to stand at room temperature overnight. The mixture was evaporated to dryness and the solid residue crystallised from methanol to give 0.14 g. of 1-[3-(2-guanidinothiazol-4-yl)cyclohexylamino]-1-(2-methoxyethylamino)-2-nitroethylene, m.p. 234°–236° (decomp.).

EXAMPLE 8

To a solution of 2-guanidino-4-(3-aminocyclohexyl)-thiazole (0.3 g.) in ethanol (30 ml.) was added 2-methyl-1-nitroisothiourea (0.2 g.) and the mixture allowed to stand overnight at room temperature. The residue, obtained on evaporation of the reaction mixture, was subjected to preparative thin layer chromatography on silica gel GF plates (Uniplate, Analtech Inc. Delaware, USA) using chloroform:methanol:ammonia (s.g. 0.88) 80:20:0.5 v/v/v for development. Elution of the appropriate region of the chromatogram with hot ethanol and evaporation of the solvent gave a glass-like material. This was dissolved in a small volume of ethanol and the solution treated with a solution of maleic acid in acetone. The resulting solution was diluted with ether to give 2-guanidino-4-[3-(2-nitroguanidino)cyclohexyl] thiazole maleate hemihydrate (0.12 g.) which was obtained as an amorphous solid. The n.m.r. spectrum in $d_6$ dimethylsulphoxide included resonances at 1.2 (brm), 1.8 (brm), 2.7 (m) 3.5(m) 6.11(s-maleic acid olefinic protons), 6.9(s), 8.05 (m) and 8.14 (brs).

EXAMPLE 9

A solution of 2-guanidino-4-(3-aminocyclohexyl)-thiazole (0.5 g.) in methanol (10 ml.) was treated with 1,2-dimethoxycyclobutene-3,4-dione (0.31 g.) in methanol (5 ml) and mixture allowed to stand at room temperature for 16 hours. The product, 1-[3-(2-guanidinothiazol-4-yl)cyclohexylamino]-2-methoxycyclobutene-3,4-dione, was collected and obtained crystalline by concentration of a solution in methanol/chloroform. The n.m.r. spectrum in $d_6$ dimethylsulphoxide included resonances at 1.2 (m) 1.8 (m), 4.30 (s), 6.24 (s), 6.79 (brs) and 8.6 (m).

EXAMPLE 10

To a solution of 2-(2-methylguanidino)-4-(3-aminocyclohexyl)thiazole (0.5 g.) in methanol (15 ml.) was added dimethyl(cyanoimido)dithiocarbonate (0.3 g.) and the resulting solution allowed to stand at room temperature overnight. Concentration of the reaction mixture gave 2-(2-methylguanidino)-4-[3-(3-cyano-2-methylisothioureido)cyclohexyl]thiazole, m.p. 200°–204° (decomp.).

The 2-(2-methylguanidino)-4-(3-aminocyclohexyl)thiazole used as starting material may be prepared as follows:

To a solution of (N-methylamidino)thiourea (1.5 g.) in hot ethanol (60 ml.) was added 1-chloroacetyl-3-phthalimidocyclohexane (3 g.) in hot ethanol (180 ml.) and the solution heated under reflux for 1 hour. The reaction mixture was concentrated to 25 ml., diluted with ether until just turbid and the 2-(2-methylguanidino)-4-(3-phthalimidocyclohexyl)thiazole hydrochloride (4.3 g.) collected.

A solution of this material (3.5 g.) in methanol (20 ml.) was treated with 3 N sodium hydroxide (10 ml.) and heated under reflux for 15 minutes. The pH of the reaction mixture was adjusted to 3 with 3 N hydrochloric acid and reflux continued for a further 15 minutes. After repetition of this procedure (pH 12 for 15 minutes then pH 3 for 15 minutes) the reaction mixture was concentrated, made strongly basic with 3 N sodium hydroxide, and extracted with ethyl acetate (3×50 ml.). Concentration of the water-washed, dried (magnesium sulphate) solution gave 2-(2-methylguanidino)-4-(3-aminocyclohexyl)thiazole (1.4 g.).

EXAMPLE 11

To a suspension of 2-(2-methylguanidino)-4-[3-(cyano-B 2-methylisothioureido)cyclohexyl]thiazole (0.4 g.) in ethanol (20 ml.) was added 20 ml. of a solution of methylamine in ethanol (33% w/v) and the resulting solution allowed to stand overnight at room temperature. The residue obtained on evaporation of the reaction mixture was subjected to preparative thin layer on silica gel GF plates using chloroform/methanol/ammonia (s.g. 0.88) 85:15:0.5 v/v/v for development. Elution of the appropriate region of the chromatograms with hot ethanol/chloroform 50:50 v/v gave a glass-like material which was dissolved in ethanol (1 ml.). To this solution was added a solution of maleic acid in acetone and the resulting solution was diluted with ether to precipitate 2-(2-methylguanidino)-4-[3-(2-cyano-3-methylguanidino)cyclohexyl]thiazole maleate. The n.m.r. spectrum in $d_6$ dimethylsulphoxide included resonances at 1.2 (m), 1.8 (m), 2.68 (d) 2.9 (d), 3.5 (m), 6.0 (s maleic acid olefinic protons), 6.5 (d), 6.77 (s), 6.8 (d) and 8.2 (br s).

EXAMPLE 12

To a solution of 2-(2-methylguanidino)-4-(3-aminocyclohexyl)thiazole (0.3 g.) in ethanol (50 ml.) was added methylisothiocyanate (0.1 g.) and the solution heated under reflux for 2 hours. Evaporation of the reaction mixture and crystallisation of the residue from methanol/ethyl acetate gave 2-(2-methylguanidino)-4-[3-(3-methylthioureido)cyclohexyl]thiazole (0.35 g.), m.p. 214°–215° (decomp.).

EXAMPLE 13

To a solution of 2-(2-methylguanidino)-4-(3-aminocyclohexyl)thiazole (0.2 g.) in acetonitrile (20 ml.) was added 1,1-di(methylthio)-2-nitroethylene (0.125 g.) and the mixture heated under reflux for 7 hours. The reaction mixture was evaporated to dryness and the residue of 1-[3-[2-(2-methylguanidino)thiazol-4-yl]cyclohexylamino]-1-methylthio-2-nitroethylene, dissolved in ethanol (20 ml.), was treated with 20 ml. of a solution of methylamine in ethanol (33% w/v). The reaction mixture was allowed to stand overnight. Evaporation of the solvent and recrystallisation of the residue from methanol gave 1-[3-[2-(2-methylguanidino)thiazol-4-yl]cyclohexylamino]-1-methylamino-2-nitroethylene, m.p. 164°–174° (decomp.).

EXAMPLE 14

To a solution of 1-[3-(2-guanidinothiazol-4-yl)cyclohexylamino]-2-methoxycyclobutene-3,4-dione in 30 ml of methanol/chloroform (50:50 v/v) was added a solution of 4(5)-(2aminoethyl)thiomethyl-5(4)-methylimidazole hydrochloride (0.16 g.) and triethylamine (0.3 g.) in methanol (10 ml.) and the resulting solution was heated under reflux for 16 hours. The reaction mixture was evaporated to dryness and the residue, dissolved in methanol (6 ml.), was added with stirring to cold water (25 ml.). The precipitated white solid was collected, washed with water (5 ml.) and dried to give 1-[3-(2-guanidinothiazol-4-yl)cyclohexylamino]-2-[2-[(5(4)-methylimidazol-4(5)-yl)methylthio]ethylamino]cyclobutene-3,4-dione. The n.m.r. spectrum in $d_6$ dimethylsulphoxide included resonances at 1.2 (m); 1.8 (m); 2.6 (t); 6.26 (s); 6.81 (br s); 7.34 (s); 7.5 (m).

EXAMPLE 15

To a solution of 1-[3-(2-guanidinothiazol-4-yl)cyclohexylamino]-2-methoxycyclobutene-3,4-dione (0.19 g.) in 35 ml. of methanol/chloroform (50:50 v/v) was added 2-(p-chlorophenyl)ethylamine (0.18 g.) and the resulting mixture allowed to stand at room temperature for 5 hours. After heating under reflux for 2.5 hours the reaction mixture was cooled and the precipitated buff-coloured solid collected to give 1-[3-(2-guanidinothiazol-4-yl)cyclohexylamino]-2-[2-(p-chlorophenyl)ethylamino]cyclobutene-3,4-dione. The n.m.r. spectrum in $d_6$ dimethylsulphoxide included resonances at 1.2 (m), 1.8 (m), 2.5 (t), 3.7 (m), 6.24 (s), 6.78 (br s).

EXAMPLE 16

To a stirred solution of 2-guanidino-4-(3-aminocyclopentyl)thiazole (0.5 g.) in methanol (5 ml.) was added dimethyl(cyanoimido)dithiocarbonate (0.32 g.) and the mixture stirred overnight. The reaction mixture was diluted with water and extracted with ethyl acetate (5×50 ml.). Evaporation of the dried (magnesium sulphate) extract gave an orange residue (0.54 g.) of 2-guanidino-4-[3-(2-cyano-3-methylisothioureido)cyclopentyl]thiazole. This residue (0.1 g.) in ethanol (5 ml.) was treated with 10 ml. of a solution of methylamine in ethanol (33% w/v) and the mixture allowed to stand overnight. The residue obtained on evaporation of the solvent was dissolved in ethanol (1 ml.) and treated with an ethanolic solution of maleic acid. On standing there was deposited crystalline 2-guanidino-4-[3-(2-cyano-3-methylguanidino)cyclopentyl]thiazole maleate, m.p. 161°–164° (decomp.).

The 2-guanidino-4-(3-aminocyclopentyl)thiazole used as starting material may be prepared as follows:

A solution of cis-3-aminocyclopentane carboxylic acid hydrochloride (8.5 g.) in water (85 ml.) was treated with anhydrous sodium carbonate (5.5 g.) and carbethoxyphthalimide (11.3 g.) and the mixture stirred at room temperature for 2 hours. The solution was filtered, the pH of the filtrate adjusted to 3 with concentrated hydrochloric acid and the precipitated 3-phthalimidocyclopentane carboxylic acid collected, washed with water and dried, m.p. 137°–140°.

To this acid (7.2 g.) was added thionyl chloride (15 ml.) and the mixture heated under reflux for 1.5 hours. After evaporation of excess thionyl chloride, the residue was treated with toluene and again evaporated to dryness to give 3-phthalimido cyclopentanoyl chloride.

This acid chloride was dissolved in dry ether (100 ml.) and added to a solution of diazomethane (3 g.) (prepared from 'Diazald') in dry ether (500 ml.) at −60°. The mixture was allowed to stand at ambient temperature for 16 hours. The filtered reaction mixture was evaporated under reduced pressure at 30° and the residual oil dissolved in acetone (20 ml.). To this solution was added concentrated hydrochloric acid, dropwise, until evolution of nitrogen ceased. The reaction mixture was poured into water (20 ml.) with stirring and the solid which precipitated was collected and crystallised from ether to give 1-chloroacetyl-3-phthalimidocyclopentane (6.4 g.), m.p. 118°–120°.

This chloroacetone (4.4 g.) in hot ethanol (50 ml.) was treated with a hot solution of amidinothiourea (1.77 g.) in ethanol (100 ml.), and the mixture heated under reflux for 1 hour. After concentration to 20 ml. and cooling there was precipitated 2-guanidino-4-(3-phthalimidocyclopentyl)thiazole hydrochloride m.p. 250°–255° (5.6 g.).

This compound (2 g.) was suspended in methanol (25 ml.) and treated with 10% w/v aqueous sodium hydroxide until the solution was strongly basic. This solution was heated under reflux for 15 minutes and the pH readjusted to about 1 with concentrated hydrochloric acid and heating under reflux continued for 30 minutes. This process of heating under reflux at pH 12 followed by a 30 minute period of heating under reflux at pH 3 was repeated twice. The final acidic reaction mixture was evaporated to dryness and the residue treated with water (60 ml.) and insoluble material removed by filtration. The filtrate was extracted with ethyl acetate (4×30 ml.), the aqueous layer evaporated to dryness and the residue treated with warm ethanol (100 ml.) The ethanolic solution was filtered and evaporated to dryness to give 2-guanidino-4-(3-aminocyclopentyl)thiazole hydrochloride as a brown oil. This material (0.7 g.) in methanol (10 ml.) was treated with a solution of potassium hydroxide (0.31 g.) in methanol (10 ml.) and the mixture evaporated to dryness. The residue was treated with warm ethanol and the mixture filtered. Evaporation of the ethanolic filtrate gave 2-guanidino-4-(3-aminocyclopentyl)thiazole as an orange-red gum.

EXAMPLE 17

To a solution of 2-guanidino-4-(3-aminocyclopentyl)-thiazole (0.53 g.) in ethanol (10 ml.) was added 1,1-di(-methylthio)-2-nitroethylene (0.39 g.). The mixture was allowed to stand at room temperature for 2.2 hours and then heated under reflux for 3.5 hours. On cooling, a solid, 1-[3-(2-guanidinothiazol-4-yl)cyclopentylamino]-1-methylthio-2-nitroethylene, separated and was collected (0.5 g.), m.p. 190°–195° (decomp.). This solid (0.3 g.) was added to 20 ml. of a solution of methylamine in ethanol (33% w/v) and the mixture stirred at room temperature overnight (solution occurred within approximately 30 minutes). The reaction mixture was evaporated to dryness and the residue subjected to preparative thin layer chromatography on silica gel GF plates (Uniplate, Analtech Inc., Delaware, U.S.A.), using chloroform/methanol/ammonia (s.g. 0.88) 100:10:0.5 v/v/v for development. Elution of the appropriate region of the chromatogram with ethanol/chloroform (3:1 v/v) and crystallisation of the extracted material from ethanol gave 1-[3-(2-guanidinothiazol-4-yl)cyclopentylamino]-1-methylamino-2-nitroethylene, m.p. 226°–230° (decomp.).

EXAMPLE 18

A solution of 1-[3-(2-guanidinothiazol-4-yl)cyclohexylamino]-2-methoxycyclobutene-3,4-dione (0.25 g.) in warm methanol/chloroform (50:50 v/v) (50 ml.) was treated with 14 ml. of a solution of methylamine in ethanol (33% w/v) and the resulting solution allowed to stand at room temperature for 2 hours. Concentration of the reaction mixture gave a crystalline solid (0.21 g.) which was collected and washed with a small volume of methanol to give 1-[3-(2-guanidinothiazol-4-yl)cyclohexylamino]-2-methylaminocyclobutene-3,4-dione, obtained as the hemihydrate, m.p. 263°–268° (decomp.).

EXAMPLE 19

A solution of 1-[3-(2-guanidinothiazol-4-yl)cyclohexylamino]-1-methylthio-2-nitroethylene (0.25 g.) in 50 ml. of a warm mixture of methanol/chloroform (50:50 v/v) was treated with ethanolamine (0.5 ml.). After standing at room temperature for 16 hours the reaction mixture was heated under reflux for 8 hours. On concentration of the reaction mixture a white solid precipitated which on crystallisation from a large volume of methanol afforded 0.16 g. of 1-[3-(2-guanidinothiazol-4-yl)cyclohexylamino]-1-(2-hydroxyethylamino)-2-nitroethylene, m.p. 216°–218° (decomp.).

EXAMPLE 20

To a solution of 1-[3-(2-guanidinothiazol-4-yl)cyclohexylamino]-2-methoxycyclobutene-3,4-dione (0.1 g.) in 15 ml. of methanol/chloroform (50:50 v/v) was added a solution of 2-guanidino-4-(3-aminocyclohexyl)-thiazole (0.07 g.) in methanol (3 ml.) and the resulting solution was allowed to stand at room temperature for 6 hours. After heating under reflux for 6 hours, the reaction mixture was concentrated and cooled to give, as a white amorphous solid, 1,2-bis[3-(2-guanidinothiazol-4-yl)cyclohexylamino]cyclobutene-3,4-dione. The carbon-13 magnetic resonance spectrum ($\delta$ relative to tetramethylsilane) in $d_6$ DMSO included one carbon singlets at 181.9, 175.0 167.0, 156.8, 155.4, 100.3, 52.4 and a series of signals from 52.4 to 24.1 (including resonances attributable to solvent) p.p.m.

EXAMPLE 21

To a solution of 1-[3-(2-guanidinothiazol-4-yl)-cyclohexylamino]-2-methoxycyclobutene-3,4-dione (0.35 g.) in 60 ml. of methanol/chloroform (50:50 v/v) was added 1,4-diaminobutane (0.044 g.) in methanol (1 ml.). The solution was heated under reflux for 16 hours during which time a precipitate formed. The reaction mixture was cooled and the solid precipitate collected and washed with methanol (1 ml.) and ether (2 ml.) to give, as an off-white powder, 1,4-bis{1-[3-(2-guanidinothiazol-4-yl)cyclohexylamino]-3,4-dioxocyclobutenylamino}butane. The carbon-13 magnetic resonance spectrum ($\delta$ relative to tetramethylsilane) in $d_6$-DMSO included one carbon singlets at 182.3, 174.8, 167.7, 167.0, 156.7, 155.3, 100.3 and 52.4 together with a series of singlets from 42.9 to 24.0 p.p.m. (the latter group of signals includes the resonances due to the solvent).

EXAMPLE 22

To a solution of 1-[3-(2-guanidinothiazol-4-yl)cyclohexylamino]-2-methoxycyclobutene-3,4-dione (0.3 g.) in 30 ml. of methanol/chloroform (50:50 v/v) was added a solution of 2-guanidino-4-[(2-aminoethyl)thiomethyl]thiazole hydrochloride (0.27 g.) and triethylamine (0.4 g.) in methanol (30 ml.) and the resulting solution was heated under reflux for 16 hours. The reaction mixture was evaporated to dryness and the residue dissolved in methanol (7 ml.). To this solution was dropwise added cold water until gummy material started to deposit. The supernatant liquid was then poured into cold water (20 ml.) and the resulting suspension stirred for 0.5 hours to effect granulation. The solid material was collected, washed with water and dried to give 1-[3-(2-guanidinothiazol-4-yl)cycohexylamino]-2-{2-[(2-guanidinothiazol-4-yl)methylthio]ethylamino}cyclobutene-3,4-dione. The n.m.r. spectrum in $d_6$-dimethylsulphoxide included the following signals: 6.85 (8H, s), 6.51 (1H, s), 6.28 (1H, s), 3.64 (2H, s on top of m).

EXAMPLE 23

To a solution of 1-[3-(2-guanidinothiazol-4-yl)cyclohexylamino]-2-methoxycyclobutene-3,4-dione (0.25 g.) in 50 ml. of methanol/chloroform (50:50 v/v) was added 3-aminoethylpyridine (0.12 g.) and the resulting solution allowed to stand at room temperature overnight. The reaction mixture was concentrated to half its initial volume, and cooled. The precipitated solid was collected and washed with a small volume of methanol to give 0.24 g. of 1-[3-(2-guanidinothiazol-4-yl)cyclohexylamino]-2-(3-pyridylmethylamino)cyclobutene-3,4-dione, m.p. 265°-270° (decomp.).

EXAMPLE 24

An intimate mixture of 2-guanidino-4-(3-aminocyclohexyl)thiazole (1.0 g.) and 2-methylthio-5-p-chlorobenzylpyrimid-4-one (1.1 g.) was maintained at 140°-160° for 16 hours. The resulting dark brown residue was dissolved in hot ethanol (50 ml.) and filtered to remove solid particles. The filtrate was subjected to dry-column chromatography on silica using chloroform/methanol/aqueous ammonia (s.g. 0.88) (85:15:0.1 v/v/v). The zone of the chromatogram containing the desired product was eluted with ethanol/chloroform (3:1 v/v) and the eluted material subjected to preparative thin layer chromatography on silica GF plates (Uniplate, Analtech Inc., Delaware, U.S.A.) using chloroform/methanol/aqueous ammonia (s.g. 0.88) 135:15:1 v/v/v for development. The appropriate region of the chromatogram was eluted with ethanol/chloroform (3:1 v/v) and the recovered material was crystallised from methanol to give 2-[3-(2-guanidinothiazol-4-yl)cyclohexylamino]-p-chlorobenzylpyrimid-4-one, (0.1 g.) m.p. 220°-230° (decomp.).

EXAMPLE 25

To a solution of 2-guanidino-4-(3-aminocyclohexyl)thiazole (0.21 g.) in ethanol (2.0 ml.) was added ethyl N-cyanoacetimidate (0.1 g.) and the stirred mixture allowed to stand at room temperature overnight. The residue obtained by evaporation of the solvent was subjected to preparative thin layer chromatography on silica gel GF plates (Uniplate, Analtech Inc. Delaware, U.S.A.) using chloroform/methanol/aqueous ammonia (s.g. 0.88) 120:30:1 v/v/v for development. The appropriate region of the chromatograms was eluted with ethanol/chloroform (3:1 v/v) and the recovered material crystallised from ethanol to give 2-guanidino-4-[3-(N-cyanoacetamidino)cyclohexyl]thiazole (0.13 g.) m.p. 248°-254° (decomp).

EXAMPLE 26

To a solution of 2-guanidino-4-(3-aminocyclopentyl)thiazole (0.3 g.) in ethanol (5 ml.) was added methyl isothiocyanate (0.15 g.) and the mixture heated under reflux for 1 hour. The reaction mixture was evaporated to dryness and the residue subjected to preparative thin layer chromatography on silica gel GF plates (Uniplate, Analtech Inc., Delaware, U.S.A.) using chloroform/methanol/aqueous ammonia (s.g. 0.88) 135:15:1 v/v/v for development. The appropriate region of the chromatogram was eluted with warm ethanol/chloroform (3:1 v/v) and the extract evaporated to give 2-guanidino-4-[3-(3-methylthioureido)cyclopentyl]thiazole as a light brown glass. The n.m.r. spectrum in $d_6$ dimethyl sulphoxide included signals at 1.2-2.2 (m) 2.8 (d, 3H) 4.2 (br m, 1H), 6.27 (s, 1H) and 6.78 (br s, 4H).

EXAMPLE 27

To a solution of 2-guanidino-4-(3-aminocyclohexyl)thiazole (0.36 g.) in ethanol (7 ml.) was added dimethyl(methylsulphonylimido)dithiocarbonate (0.3 g.) in methanol (7 ml.) and mixture allowed to stand at room temperature overnight. The crystalline precipitate (0.56 g.) was collected and washed with a little methanol to give 2-guanidino-4-[3-(3-methylsulphonyl-2-methylisothioureido)cyclohexyl]thiazole, m.p. 204°-206° (decomp.).

EXAMPLE 28

A solution of 2-guanidino-4-[3-(3-methylsulphonyl-2-methylisothioureido)cyclohexyl]thiazole (0.25 g.) in methanol/chloroform 50:50 v/v (15 ml.) was treated with 20 ml. of 33% w/v methylamine in ethanol and the mixture allowed to stand at room temperature overnight. Evaporation of the solvent gave a gum which was dissolved in methanol (1 ml.) and to this solution was added an excess of maleic acid in acetone. The resulting solution was diluted with ether until crystallisation occurred, giving 2-guanidino-4-[3-(2-methylsulphonyl-3-methylguanidino)cyclohexyl]-thiazole hydrogen maleate monohydrate, m.p. 184°-187° (decomp).

EXAMPLE 29

To a solution of 2-guanidino-4-(3-aminocyclohexyl)thiazole (0.35 g.) in methanol (5 ml.) was added a solution of dimethyl (3-pyridylsulphonylimido)dithiocarbonate (0.3 g.) in ethanol (5 ml.). The mixture was warmed to give a solution and then allowed to reach room temperature and to stand overnight. The crystalline precipitate was collected and washed with a little methanol to give 2-guanidino-4-{3-[2-methyl-3-(3-pyridylsulphonyl)isothioureido]cyclohexyl}thiazole (0.31 g.), m.p. 185°-187° (decomp.).

EXAMPLE 30

To a solution of 2-guanidino-4-{3-[2-methyl-3-(3-pyridylsulphonyl)isothioureido]cyclohexyl}thiazole (0.2 g.) in a warm mixture of methanol (10 ml.) and chloroform (5 ml.) was added 20 ml. of 33% w/v methylamine in ethanol and the resulting solution allowed to stand at room temperature for 5 hours. The residue obtained on evaporation of the solvent was dissolved in methanol (0.5 ml.) and to this solution was added an excess of maleic acid in acetone. Addition of ether to this solution precipitated crystalline 2-guanidino-4-{3-[2-methyl-3-(3-pyridylsulphonyl)guanidino]cyclohexyl}thiazole hydrogen maleate monohydrate, m.p. 172°–174° (decomp.).

EXAMPLE 31

To a solution of 2-guanidino-4-[3-(3-cyano-2-methylisothioureido(cyclohexyl]thiazole (1.1 g.) in ethanol/chloroform 50:50 v/v (50 ml.) was added ethylenediamine (3 ml.) and the solution heated under reflux for 48 hours. The residue obtained by evaporation of the solvents was triturated with water (50 ml.) and the aqueous layer decanted. The dried residue crystallised on trituration with methanol to give 2-guanidino-4-{3-[3-cyano-2-(2-aminoethyl)guanidino]cyclohexyl}-thiazole whose crystals contained 0.75 mol water of crystallisation, m.p. 203°–205° (0.18 g.). A further quantity (0.23 g.) of this compound separated from the aqueous decantate on standing.

EXAMPLE 32

To a solution of 2-guanidino-4-{3-[3-cyano-2-(2-aminoethyl)guanidino]cyclohexyl}thiazole (0.5 g.) in methanol (30 ml.) was added o-chlorobenzoyl chloride (0.4 g.) and the mixture allowed to stand at room temperature for 16 hours. The residue obtained by evaporation of the solvent was partitioned between ethyl acetate (100 ml.) and water (20 ml.) The organic layer was isolated, washed with water (20 ml), dried (magnesium sulphate) and evaporated. The residue was subjected to preparative thin layer chromatography on Merck 60 F-254 plates using chloroform/methanol/aqueous ammonia (s.g. 0.88) 80:20:0.1 v/v/v for development. The appropriate zone of the chromatogram was isolated and extracted with hot ethanol/chloroform 50:50 v/v (200 ml.) and the residue obtained on evaporation of the solvents was dissolved in methanol. To this solution was added an excess of maleic acid in ether followed by a further amount of ether until precipitation began. The white powder precipitate (0.2 g.) was washed with ether to give 2-guanidino-4-{3-[3-cyano-2-(2-(2-chlorobenzoylamino)ethyl)guanidino]cyclohexyl}-thiazole hydrogen maleate, m.p. 158°–165° (decomp.).

EXAMPLE 33

To a solution of 2-guanidino-4-{3-[3-cyano-2-(2-aminoethyl)guanidino]cyclohexyl}thiazole (0.525 g.) in methanol was added benzenesulphonyl chloride (0.3 g.) and the mixture was allowed to stand at room temperature for 16 hours. The residue obtained on evaporation of the solvent was partitioned between ethyl acetate (100 ml.) and 2 N sodium hydroxide (20 ml.). The aqueous alkaline layer was extracted with a further quantity (100 ml.) of ethyl acetate and the organic extracts combined, washed with water (50 ml.) and dried (magnesium sulphate). The residue obtained on evaporation of the ethyl acetate was subjected to preparative thin layer chromatography on Merck 60 F-254 plates using chloroform/methanol/aqueous ammonia (s.g. 0.88) 70:30:0.1 v/v/v for development. The appropriate zone of the chromatogram was isolated and extracted with hot ethanol/chloroform 50/50 v/v (200 ml.). The residue obtained by evaporation of the solvents was dissolved in methanol (1 ml.) and to this solution was added an excess of maleic acid in ether. Addition of a further amount of ether completed precipitation. The residue obtained by decantation of the supernatant was crystallised from methanol to give 0.18 g. of 2-guanidino-4-{3-[3-cyano-2-(2-benzenesulphonylamino)ethyl)guanidino]cyclohexyl}thiazole hydrogen maleate hemihydrate, m.p. 140°–144°.

EXAMPLE 34

To a solution of 2-guanidino-4-(3-aminocyclohexyl)-thiazole (0.5 g.) in tetrahydrofuran (20 ml.) was added thiocarbonyldiimidazole (0.4 g.) in tetrahydrofuran (15 ml.) in portions over 15 minutes. After 30 minutes at room temperature the solvent was evaporated and the residue partitioned between ethyl acetate (100 ml.) and water (20 ml.). The organic layer was separated, washed with water (20 ml.) and dried (magnesium sulphate) concentrated to small volume and petroleum ether (b.p. 40°–60°) added whereupon crystals of the 2-guanidino-4-(3-isothiocyantocyclohexyl)thiazole were deposited (0.35 g.). To this material in methanol (5 ml.) was added 2,2,2-trifluoroethylamine hydrochloride (0.4 g.) and triethylamine (0.4 g.) and the mixture allowed to stand at room temperature in a stoppered vessel for 2 days. The residue obtained on evaporation of the solvent was partitioned between ethyl acetate (100 ml.) and 2 N hydrochloric acid (20 ml.) and the ethyl acetate layer separated, washed with water (2×20 ml.), dried (magnesium sulphate) and evaporated. The residue was subjected to preparative thin layer chromatography on Merck 60 F-254 plates using chloroform/methanol/aqueous ammonia (s.g. 0.88) 80:20:01 v/v/v for development. The appropriate zone of the chromatogram was isolated and extracted with hot ethanol/chloroform 50:50 v/v (200 ml.) and the extract evaporated to give a gummy residue. This residue was dissolved in acetone (1 ml.) and to the solution was added an excess of maleic acid in ether. The white amorphous solid which precipitated collected, and washed with ether to give 0.12 g. of 2-guanidino-4-{3-[3-(2,2,2-trifluoroethyl)thioureido]cyclohexyl}thiazole hydrogen maleate, m.p. 148°–150°.

EXAMPLE 35

To a solution of 2-guanidino-4-(3-isothiocyanatcyclohexyl)thiazole (0.6 g.), prepared as described in Example 34, in methanol (10 ml.) was added 4-(3-aminopropyl)imidazole dihydrochloride (0.4 g.) and triethylamine (0.6 ml.) in methanol (15 ml.) and the mixture allowed to stand at room temperature for 7 days. The reaction mixture was diluted with water (20 ml.) and extracted with ethyl acetate (4×60 ml.). The dried (magnesium sulphate) solution was evaporated to dryness and the residue in methanol (1 ml.) treated with an excess of maleic acid in acetone. Dilution of the resulting solution with ether precipitated an amorphous solid (720 mg.) which was collected and washed with ether to give 2-guanidino-4-{3-[3-(3-[imidazol-4-yl]propyl)-thioureido]cyclohexyl}thiazole dihydrogen maleate monohydrate, m.p. 130°–134°.

EXAMPLE 36

To a solution of 2-guanidino-4-[3-(3-methylthioureido)cyclohexyl]thiazole (0.5 g.) in dimethylformamide (2 ml.) was added a solution of silver nitrate (0.6 g.) in water (2 ml.). After 15 minutes at room temperature hydrogen sulphide was passed into the solution and the precipitated silver sulphide removed by filtration. The filtrate was diluted with 2 N hydrochloric acid (15 ml.) and the mixture extracted with ethyl acetate (50 ml.). The aqueous layer was then adjusted to pH 12 with 2 N sodium hydroxide and extracted with ethyl acetate (2×50 ml.). The water washed and dried (magnesium sulphate) ethyl acetate solution was evaporated and the residue crystallised from methanol to give 0.23 g. of 2-guanidino-4-[3-(3-methylureido)cyclohexyl]thiazole, m.p. 194°–196° (decomp.).

EXAMPLE 37

To a solution of 2-guanidino-4-{3-[3-(2,2,2-trifluoroethyl)thioureido]cyclohexyl}thiazole (0.5 g.) in dimethylformamide (4 ml.) was added silver nitrate (0.5 g.) in water (2 ml.) After 30 minutes at room temperature hydrogen sulphide was passed into the solution and precipitated silver sulphide removed by filtration. The filtrate was evaporated and the residue suspended in N sodium hydroxide (20 ml.) and the mixture extracted with ethyl acetate (2×50 ml.). Evaporation of the water washed, dried (magnesium sulphate) ethyl acetate extract gave a residue which was subjected to preparative thin layer chromatography on Merck 60 F-254 plates using ethyl acetate/methanol/water 60:10:10 v/v/v for development. The appropriate zone of the chromatrogram was isolated and extracted with hot ethanol/chloroform 50:50 v/v (200 ml.). Evaporation of the solvents gave a residue which was dissolved in methanol (0.5 ml.) and treated with an excess of maleic acid in acetone/ether 50:50 v/v, whereupon there was deposited crystalline 2-guanidino-4-{3-[3-(2,2,2-trifluoroethyl)ureido]cyclohexyl}thiazole hydrogen maleate monohydrate, m.p. 220°–222°.

EXAMPLE 38

To a solution of 2-guanidino-4-[3-(3-methylthioureido)cyclohexyl]thiazole (0.8 g.) in dimethylformamide (4 ml.) was added aqueous ammonium hydroxide (s.g. 0.88) (2 ml.) followed by silver nitrate (0.85 g.) in dimethylformamide (4 ml.). After 1 hour at room temperature hydrogen sulphide was passed into the solution and the precipitated silver sulphide removed by filtration. The filtrate was evaporated and the residue in water (30 ml.) basified with aqueous ammonium hydroxide (s.g. 0.88) and extracted with ethyl acetate (50 ml.). The aqueous fraction was evaporated to dryness and the residue crystallised from methanol to give 0.35 g. of 2-guanidino-4-[3-(3-methylguanidino)cyclohexyl]thiazole dinitrate, m.p. 235°–237°.

EXAMPLE 39

To a solution of 2-guanidino-4-{3-[3-(2,2,2-trifluoroethyl)thioureido]cyclohexyl}thiazole (0.3 g.) in dimethyl formamide (4 ml.) was added aqueous ammonium hydroxide (s.g. 0.88) (2 ml.) and to this solution was added silver nitrate (0.29 g.) in dimethylformamide (5 ml.). After 30 minutes hydrogen sulphide was passed into the solution to complete precipitation of silver sulphide. After removal of the precipitate by filtration, the solution was evaporated to dryness and the residue partitioned between ethyl acetate (60 ml.) and water (20 ml.). The organic layer was isolated, washed with water and dried (magnesium sulphate). Evaporation of the solvent gave a gum which was dissolved in acetone (0.5 ml.) and treated with excess of maleic acid in ether. The precipitate was collected and washed with ether to give 0.12 g. of 2-guanidino-4-{3-[3-(2,2,2-trifluoroethyl)guanidino]-cyclohexyl}thiazole dihydrogen maleate hemihydrate. The n.m.r. spectrum (δ relative to tetramethylsilane) in d₆-dimethylsulphoxide:-8.2 (4H, br s), 6.82 (1H, s) and 4.2 (2H, m).

EXAMPLE 40

To a solution of 2-[2-(2-methoxyethyl)guanidino]-4-(3-aminocyclohexyl)thiazole (0.6 g.) in methanol (10 ml.) was added methylisothiocyanate (0.2 g.) and the solution allowed to stand at room temperature overnight. The gummy residue obtained on evaporation of the solvent was dissolved in methanol (0.5 ml.) and this solution was treated with an excess of maleic acid in acetone. Addition of ether precipitated a sticky white solid which was collected and triturated with a little methanol and ether to give 0.4 g. of a crystalline form of 2-[2-(2-methoxyethyl)guanidino]-4-[3-(3-methylthioureido)cyclohexyl]thiazole hydrogen maleate, m.p. 184°–186°.

The 2-[2-(2-methoxyethyl)guanidino]-4-(3-aminocyclohexyl)thiazole used as starting material may be prepared as follows:

To a solution of 1-chloroacetyl-3-phthalimidocyclohexane (3 g.) in boiling ethanol (40 ml.) was added N-[(2-methoxyethyl)amidino]thiourea (1.8 g.) in hot ethanol (40 ml.). The solution was heated under reflux for 1 hour and then concentrated to about 15 ml. and diluted with ether whereupon 2-[2-(2-methoxyethyl)guanidino]-4-(3-phthalimidocyclohexyl)thiazole hydrochloride (4.0 g.) was precipitated as a gelatinous solid. This solid (2.0 g.) was dissolved in methanol (10 ml.) and the pH of the solution adjusted to 12 with 2 N sodium hydroxide. The mixture was heated on a steam bath for 10 minutes and the pH adjusted to 3 with conc. hydrochloric acid and heating continued for 30 minutes. After a further period of heating at pH 12 (5 minutes) and pH 3 (15 minutes), the reaction mixture was poured into water and the resulting solution basified with 2 N sodium hydroxide and extracted with ethyl acetate. Evaporation of the water-washed, dried (magnesium sulphate) ethyl acetate extract gave 2-[2-(2-methoxy)-guanidino]-4-(3-aminocyclohexyl)thiazole as a straw coloured gum which was used without further purification.

EXAMPLE 41

To a solution of 2-[2-(2-methoxyethyl)guanidino]-4-(3-aminocyclohexyl)thiazole (0.55 g.) in acetonitrile (10 ml.) was added 1,1-di(methylthio)-2-nitroethylene (0.3 g.) and the solution heated under reflux for 16 hours. The residue obtained on evaporation of the solvent was dissolved in ethanol (10 ml.) and treated with 30 ml. of a solution of methylamine in ethanol (33% w/v) and the resulting solution allowed to stand at room temperature for 3 hours. Evaporation of the solvent and crystallisation of the residue from methanol gave 0.39 g. of 1-{3-[2-((2-methoxyethyl)guanidino)thiazol-4-yl]cyclohexamino}-1-methylamino-2-nitroethylene, m.p. 140°–142°.

What we claim is:
1. A guanidine derivative of the formula:

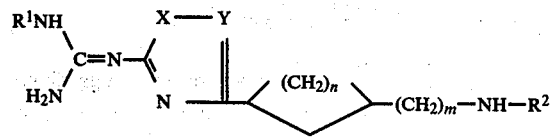

I in which X is oxygen or sulphur;

Y is nitrogen or a CH radical;

n is 1, 2, 3 or 4;

m is 0 or 1;

$R^1$ is hydrogen, alkyl of 1–6 carbons or alkoxyalkyl of 3 to 10 carbons in which the oxygen is separated from the nitrogen of the guanidine by at least two carbons;

—$R^2$ is a radical of the formula —A—B in which A is 3,4-dioxocyclobuten-1,2-dyl or C=Z in which Z is oxygen, sulphur or NCN, $NNO_2$, $CHNO_2$, $NCONH_2$, $C(CN)_2$, $NCOR^3$, $NCO_2R^3$, $NSO_2R^3$ or $NR^4$ in which $R^3$ is alkyl of 1 to 6 carbons, phenyl or pyridyl and $R^4$ is hydrogen or alkyl of 1 to 6 carbons;

B is alkyl, alkoxy or alkylthio of 1 to 6 carbons or $NHR^5$ in which $R^5$ is hydrogen or alkyl of 1 to 6 carbons, alkenyl or alkynyl of 3 to 10 carbons in which the double or triple bond is separated from the nitrogen of $NHR^5$ by at least one carbon, cycloalkyl of 3 to 6 carbons, (primary hydroxy)alkyl or (primary amino)alkyl of 2 to 6 carbons, haloalkyl of 1 to 6 carbons, alkoxyalkyl of 3 to 6 carbons in which the oxygen is separated from the nitrogen of $NHR^5$ by at least two carbons, phenylalkyl or pyridyl-3-methyl, or $R^5$ is benzoylaminoalkyl or benzenesulphonylaminoalkyl in which the alkyl part is of 2 to 6 carbons and the benzene ring carries an optional chlorine, or a radical of the formula:

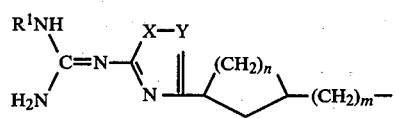  II

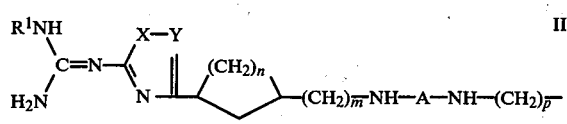  III

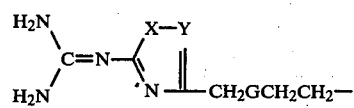  IV

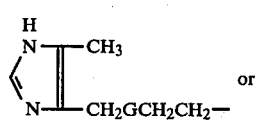  V or

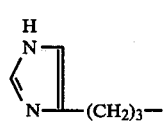  VI in which X, Y, n, m and $R^1$ have the meanings given above, p is 2 to 12 and G is sulphur or methylene; or —$R^2$ is:

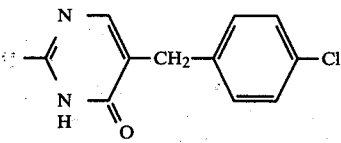  VII

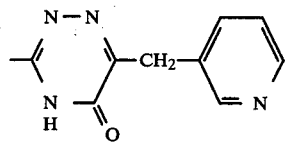  VIII or

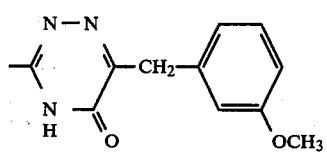  IX and the pharmaceutically-acceptable acid-addition salts thereof.

2. A guanidine derivative as claimed in claim 1 in which $R^1$ is hydrogen, methyl, ethyl, n-butyl or 2-methoxyethyl; $R^3$ is methyl, phenyl or 3-pyridyl; $R^4$ is hydrogen or methyl; B is methyl, methoxy, ethoxy or methylthio or $NHR^5$ in which $R^5$ is hydrogen, methyl, ethyl, allyl, propargyl, 2-hydroxyethyl, 2-aminoethyl, trifluoromethyl, 2-methoxyethyl, benzyl, 2-phenylethyl, 2-(4-chlorophenyl)-ethyl, pyrid-3-ylmethyl, 2-benzoylaminoethyl, 2-(2-chlorobenzoylamino)ethyl or 2-benzenesulphonylaminoethyl.

3. A guanidine derivative as claimed in claim 1 in which the groups attached to the alicyclic ring are in the cis configuration.

4. A guanidine derivative as claimed in claim 3 in which X is sulphur, Y is CH and $R^1$ is a hydrogen or 2-methoxyethyl.

5. A guanidine derivative as claimed in claim 4 in which n is 2 or 3 and m is 0.

6. A guanidine derivative as claimed in claim 5 in which —$R^2$ is —A—B in which A is C=Z in which Z is NCN, $NNO_2$, $CHNO_2$ or $NSO_2CH_3$ and B is $NHR^5$ in which $R^5$ is methyl or 2-aminoethyl.

7. A guanidine derivative as claimed in claim 1 in which —$R^2$ is a radical of the formula VII, VIII or IX given in claim 1.

8. A compound selected from the group consisting of 2-guanidino-4-[3-(2-cyano-3-methylguanidino)cyclopentyl]-thiazole, 2-guanidino-4-[3-(3-methylthioureido)cyclopentyl]thiazole, 2-guanidino-4-{3-[3-cyano-2-(2-aminoethyl)-guanidino]cyclohexyl}thiazole, 2-[2-(2-methoxyethyl)guanidino]-4-[3-(3-methylthioureido)cyclohexyl]thiazole and 1-{3-[2-((2-methoxyethyl)guanidino)thiazol-4-yl]cyclohexylamino}-1-methylamino-2-nitroethylene, and the pharmaceutically-acceptable acid-addition salt thereof.

9. A pharmaceutical composition for inhibiting gastric acid secretion comprising a guanidine derivative as claimed in claim 1 in association with a non-toxic pharmaceutically-acceptable diluent or carrier.

10. A method of inhibiting gastric acid secretion in a warm-blooded animal which comprises administering to the animal a therapeutically-effective amount of the composition of claim 9.

* * * * *